United States Patent [19]
Kayane et al.

[11] Patent Number: 5,543,310
[45] Date of Patent: Aug. 6, 1996

[54] IMMOBILIZED PHOSPHORYLASE

[75] Inventors: Shigeto Kayane; Takashi Kawai; Masaru Sakata; Takashi Imamura; Masanobu Tanigaki, all of Wakayama-ken; Tomihiro Kurosaki, Osaka-fu, all of Japan

[73] Assignee: Kao Corporation, Tokyo, Japan

[21] Appl. No.: 113,743

[22] Filed: Aug. 31, 1993

Related U.S. Application Data

[63] Continuation of Ser. No. 742,532, Aug. 8, 1991, abandoned, which is a continuation of Ser. No. 235,522, Aug. 24, 1988, abandoned.

[30] Foreign Application Priority Data

Sep. 2, 1987 [JP] Japan ................... 62-219674

[51] Int. Cl.$^6$ .............. C12N 11/08; C12N 9/10
[52] U.S. Cl. ............ 435/180; 435/193; 435/194; 435/105; 435/181
[58] Field of Search ................. 435/176, 180, 435/182, 181, 193, 199, 105

[56] References Cited

U.S. PATENT DOCUMENTS

| | | | |
|---|---|---|---|
| 4,451,582 | 5/1984 | Denzinger | 435/41 |
| 4,686,243 | 8/1987 | Keil et al. | 435/180 |

FOREIGN PATENT DOCUMENTS

| | | | |
|---|---|---|---|
| 58-31990 | 2/1983 | Japan | . |

OTHER PUBLICATIONS

Daurat–Larroque et al, "Enzyme Reactors . . . " *J. of App. Biochem 4* pp. 133–152 (1982).
Kumar et al., Indian J. of BioChem & Biophys. vol. 18, pp. 114–119, 1981.
Worthington Enzymes Manual, 1988.
Chem. Abs., vol. 110, no. 11, p. 341, abstract no. 91272u (Mar. 13, 1989).
Chem. Abs., vol. 95, no. 3, p. 290, abstract no. 20490z (Jul. 20, 1981).
Chem. Abs., vol. 98, no. 5, p. 534, abstract no. 33021j (Jan. 31, 1983).
Patent Abstract of Japan, vol. 7, no. 108 (C–165) [1253] (May 11, 1983).
Mosbach et al., *Febs Lett.*, vol. 42, 1974 pp. 200–204.
Alltech Assoc. Catalog 200, p. 615, 1989.

*Primary Examiner*—Irene Marx
*Attorney, Agent, or Firm*—Oblon, Spivak, McClelland, Maier & Neustadt, P.C.

[57] ABSTRACT

A process for preparing glucose-1-phosphate from an α-glucan and orthophosphate using a phosphorylase immobilized onto an anion-exchange resin is disclosed. The anion-exchange resin used is a synthetic polymer resin into which an anion exchange group; a primary to quarternary ammonium group, a phosphonium group, or a sulfonium group, is introduced. This type of immobilized phosphorylase ensures (i) an effective utilization of phosphorylase, (ii) a higher reactivity of a higher absorbance of the phosphorylase to the resin, (iii) an excellent phosphorylase activity retention performance, and (iv) a higher physical strength of the resin.

5 Claims, No Drawings

IMMOBILIZED PHOSPHORYLASE

This application is a Continuation of application Ser. No. 07/742,532, filed on Aug. 8, 1991, which was a Continuation of application Ser. No. 07/235,522, filed on Aug. 24, 1988, both now abandoned.

BACKGROUND OF THE INVENTION

1. Field of the Invention

This invention relates to a process for preparing glucose-1-phosphate using an immobilized enzyme, and, more particularly, to a process for preparing, by the use of an immobilized enzyme, glucose-1-phosphate, which is a compound produced at the initial stage of a series of glycolysis reactions and is useful as an antibacterial agent for pharmaceutical applications, an antitumor agent (a platinum complex), a heart disease curing agent (amine salt), and the like.

2. Description of the Background

Conventionally, various processes for preparing glucose-1-phosphate from an α-glucan (starch, glycogen, or the like) and orthophosphate using enzymatic catalytic action of a phosphorylase have been known. Examples are a method using glycogen as an α-glucan and rabbit muscle extract as an enzyme fluid [Cori et al; J. Biol. Chem., 121, 465 (1937)] and a method using potato juice as an enzyme fluid and starch as an α-glucan [C. S. Hanes; Proc. R. Soc., B129, 174 (1940)].

More specifically, glucose-1-phosphate is synthesized using a glucan and orthophosphate as substrates and acting a phosphorylase on the substrates. After the reaction, the enzyme is heat-treated to degenerate and solidify it, and then removed from the reaction system. Unreacted orthophosphate is converted into an insoluble salt such as $Mg_3(PO_4)_2$, $MgNH_4PO_4$, $Ba_3(PO_4)_2$, or the like, and removed for disposal. The unreacted glucan is removed by the use of an ion-exchange resin or by re-precipitating from an alcohol.

In these methods, however, the reaction is carried out batch-wise, requiring removal of the enzyme each time the reaction completes in the batch process. This entails a significant cost disadvantage in the industrial production.

The use of an immobilized enzyme with a phosphorylase carried onto a carrier is one of the measures for resolving this problem.

One of the processes to synthesize glucose-1-phosphate using an immobilized phosphorylase was reported by S. D. Larroque et al [J. Appl. Biochem., 4, 133 (1982)]. The report proposes immobilization of phosphorylase by combining the phosphorylase through an ionic bond onto a weakly basic anion-exchange resin which is prepared by introducing a diethylaminoethyl group into cellulose, through a hydrophobic bond onto a resin prepared by introducing an octyl group into agarose, and through a covalent bond onto a agarose which is activated by CNBr. All of these methods for immobilizing the phosphorylase, however, provide only an insufficient absorption of phosphorylase so that the immobilized enzyme exhibits only poor capability to synthesize glucose-1-phosphate. In addition, the use of polysaccharide resins in these methods involves difficulties in handling the resins, for example, in regenerating the resins. The methods are also disadvantageous in view of the production cost.

The need has therefore existed for a process for preparing glucose-1-phosphate through a more efficient use of phosphorylase, eliminating the above-mentioned problems.

In view of this situation, the inventors has undertaken extensive studies on the reaction of α-glucan and orthophosphate in the presence of an immobilized phosphorylase, and on the immobilized phosphorylase to be employed, in particular, and found that a phosphorylase carried onto a specific type of a carrier are suitable for this reaction. This finding has led to the completion of this invention.

SUMMARY OF THE INVENTION

Accordingly, an object of this invention is to provide, in a process for preparing glucose-1-phosphate from an α-glucan and orthophosphate, a process characterized by using a phosphorylase immobilized onto an anion-exchange resin comprising a synthetic polymer resin into which an anion-exchange group is introduced.

Other objects, features and advantages of the invention will hereinafter become more readily apparent from the following description.

DETAILED DESCRIPTION OF THE INVENTION AND PREFERRED EMBODIMENTS

Synthetic polymer resins used in this invention may be those of styrene-, vinyl-, propylene-, ethylene-, butadiene-, acrylonitrile-, isoprene-, acrylic acid-, methacrylic acid-, phenol-, phenol/m-phenylenediamine-, and epichlorohydrin-types. Among these, particularly preferable synthetic polymer resins are those of styrene- and vinyl types.

Given as examples of anion-exchange groups introduced into these synthetic polymer resins are primary to quaternary ammonium groups, a phosphonium group, a sulfonium group, and the like. Quaternary ammonium groups are particularly preferable anion-exchange groups.

These anion-exchange resins possess various advantages over the conventionally employed anion-exchange resins using a polysaccharide such as cellulose, dextrin, agarose, or the like as a resin. These advantages include a higher phosphorylase absorption capability, a higher glucose-1-phosphate productivity, a higher physical strength providing handling easiness, and a lower cost.

Except for the use of the phosphorylase immobilized onto the above-mentioned anion-exchange resins, the process of this invention can be performed according to the conventionally known processes for the preparation of glucose-1-phosphate using phosphorylases.

To illustrate a specific process, an immobilized phosphorylase is first prepared by mixing, through stirring or shaking, an activated anion-exchange resin, which is optionally equilibrated with a buffer solution, and a phosphorylase derived from animals, plants, or microorganisms, or a substance containing such a phosphorylase.

In this preparation, there is no specific limitation to the proportion of the phosphorylase or the substance containing the same and the anion-exchange resin. A desirable range for the proportion, however, is above 1.0 in terms of the ratio by volume of the phosphorylase/anion-exchange resin, and above 5.0 (U/g) in terms of the ratio of total activity of phosphorylase (U) and the weight of the anion-exchange resin (g). Immobilization of the phosphorylase may also be performed by passing the phosphorylase or the substance containing the same through a column packed with the anion-exchange resin.

The next step is the preparation of a mixed solvent of glucan and orthophosphate. Starch, glycogen, dextrin, amylase, or the like is used as a glucan. The glucan concentration is adjusted between 0.01 and 50% by weight, and preferably between 0.1 and 20% by weight. As the orthophosphate source, either an orthophosphate itself or orthophosphoric acid neutralized with a base may be used. The orthophosphate can also be a mixture of di- and mono-hydrogenphosphate. The concentration of the orthophosphate is adjusted between 0.01 and 5 mol/l and preferably between 0.5 and 2.0 mol/l. The pH of the solution is adjusted between 4.5 and 10, and preferably between 6.5 and 8.5. The pH adjustment, however, is difficult at a higher orthophosphate concentration. Therefore, a mixed solvent of the di- and mono-hydrogenphosphate molar ratio of 0.5/9.5–9/1, preferably of 0.5/9.5–5.5/4.5, is prepared at such a high orthophosphate concentration. There is no specific limitation to the types of the salts. Preferable salts are, however, those having a higher water solubility, and sodium or potassium salt is particularly preferable.

Finally, the phosphorylase to be immobilized is added to the mixed solution of glucan and orthophosphate thus prepared. Alternatively, the mixed solution may be passed through a column packed with the immobilized phosphorylase. The reaction is effected at a temperature of 5°–60° C., preferably 25°–40° C., to produce glucose-1-phosphate.

The other conditions such as reaction time, passage time through the column, additives to be used, the use of an antiseptic, or the like can be determined according to the purposes intended in each case.

According to the process of this invention, glucose-1-phosphate can be prepared at a low cost by the use of the phosphorylase immobilized onto specific types of anion-exchange resins, because such an immobilized phosphorylase ensures (i) an effective utilization of phosphorylase, (ii) a higher reactivity (because of a higher absorbance of the phosphorylase to the resin), (iii) an excellent phosphorylase activity retention performance, and (iv) a higher physical strength of the resin.

Other features of the invention will become apparent in the course of the following description of the exemplary embodiments which are given for illustration of the invention and are not intended to be limiting thereof.

EXAMPLES (Preparation of an immobilized phosphorylase)

To a 50–200 g of anion-exchange resin was added 700–3,000 ml of potato juice which was prepared by crushing potatoes with a juicer, followed by centrifugation. The mixture was shaken at 100 stroke/min at 25° C. for 5 hours to produce an immobilized phosphorylase. The immobilized phosphorylase had an activity of 28.0–33.9 U per gram of the resin. This value was 50% of the phosphorylase activity before immobilization. The value for the enzyme activity (U) used here is defined as the amount of the enzyme required to produce 1 μmol of a product at 30° C. in 1 minute.

The anion-exchange resin used in this example was a strong basic anion-exchange resin using a polystyrene-type polymer as a synthetic polymer resin into which trimethylammonium group was introduced.

(Quantitative analysis of glucose-1-phosphate)

The glucose-1-phosphate synthesized was quantitated by means of high performance liquid chromatography. The column used was ion-exchange column TSK gel SAX, 6 mm×15 cm, manufactured by Toyo Soda Manufacturing Co., Ltd., with the eluent, 0.5 mol/l of sodium acetate, being passed through at a rate of 1.5 ml/min. The peak was detected by means of the differential reflectometer, type SE-51, manufactured by Showa Denko Co., Ltd.

Example 1

Into 80 ml of an aqueous solution containing 12.7 g of $KH_2PO_4$ and 18.6 g of $K_2HPO_4$ was dissolved 10.0 g of 3.97 DE (dextrose equivalent) dextrin. To this solution 5.9 g (200U) of immobilized phosphorylase and 2 ml of toluene, as an antiseptic, were added. This mixture, after adjusting the total volume to 100 ml, was shaken at 40° C. for 48 hours to complete the reaction and to produce 88.4 mmol/l of glucose-1-phosphate.

Example 2

Into 80 ml of an aqueous solution containing 12.7 g of $KH_2PO_4$ and 18.6 g of $K_2HPO_4$ was dissolved 10.0 g of 3.97 DE dextrin. To this solution 11.8 g (400 U) of immobilized phosphorylase and 2 ml of toluene, as an antiseptic, were added. This mixture, after adjusting the total volume to 100 ml, was shaken at 40° C. for 48 hours to complete the reaction and to produce 114.0 mmol/l of glucose-1-phosphate.

Example 3

Into 40 ml of an aqueous solution containing 6.4 g of $KH_2PO_4$ and 9.3 g of $K_2HPO_4$ was dissolved 5.0 g of 3.97 DE dextrin. To this solution 2.98 g (400u) of the immobilized phosphorylase and 1 ml of toluene, as an antiseptic, were added. This mixture, 50 ml in volume, was shaken at 40° C. for 48 hours to complete the reaction and to produce 111.6 mmol/l of glucose-1-phosphate.

The reaction fluid was filtered to recover the immobilized enzyme, which was then added to about 40 ml of aqueous solution containing 5.0 g of 3.97 DE dextrin, 6.4 g of $KH_2PO_4$ and 9.3 g of $K_2HPO_4$. To this mixture 1 ml of toluene was added, and after adjusting the total volume to 50 ml, the mixture was reacted under shaking at 40° C. for 48 hours to produce 113.9 mmol/l of glucose-1-phosphate.

The reaction fluid thus obtained was again filtered to recover the immobilized enzyme, which was then added to about 40 ml of aqueous solution containing 5.0 g of 3.97 DE dextrin, 6.4 g of $KH_2PO_4$ and 9.3 g of $K_2HPO_4$. To this mixture 1 ml of toluene was added, and after adjusting the total volume to 50 ml, the mixture was reacted with shaking at 40° C. for 48 hours to produce 112.8 mmol/l of glucose-1phosphate.

Comparative Example

To 50 g of an anion-exchange resin which was prepared by introducing diethylaminoethyl group into regenerated cellulose was added 700 ml of potato juice prepared by crushing potatoes with a Juicer followed by centrifugation. The mixture was shaken at 100 stroke/min at 25° C. for 5 hours to produce an immobilized phosphorylase. The immobilized phosphorylase had an activity of 21.9 U per gram of the resin.

Then, 4.62 g (101 U) of this immobilized phosphorylase and an antiseptic (1 ml of toluene) was added to 5.0 g of 3.97 DE dextrin dissolved into 40 ml of aqueous solution containing 6.4 g of $KH_2PO_4$ and 9.3 g of $K_2HPO_4$. After adjusting the volume to 50 ml, the mixture was reacted with shaking at 40° C. for 48 hours to produce 112.1 mmol/l of glucose-1-phosphate.

The reaction fluid was filtered to recover the immobilized enzyme, which was then added to about 40 ml of aqueous solution containing 5.0 g of 3.97 DE dextrin, 6.4 g of $KH_2PO_4$ and 9.3 g of $K_2HPO_4$. To this mixture 1 ml of toluene was added, and after adjusting the total volume to 50 ml, the mixture was reacted with shaking at 40° C. for 48 hours to produce 88.2 mmol/l of glucose-1-phosphate.

The reaction fluid thus obtained was again subjected to filtration to recover the immobilized enzyme, which was then added to about 40 ml of aqueous solution containing 5.0 g of 3.97 DE dextrin, 6.4 g of $KH_2PO_4$ and 9.3 g of $K_2HPO_4$. To this mixture 1 ml of toluene was added, and after adjusting the total volume to 50 ml, the mixture was reacted with shaking at 40° C. for 48 hours to produce 73.2 mmol/l of glucose-1-phosphate.

Example 4

A column was packed with 167.4 g (4989 U) of immobilized phosphorylase and warmed by circulating water at a temperature of 40° C. around it. Into this column was charged at a rate of 6.6 ml/hour and a space velocity of 0.024/hour an aqueous solution containing 10 g/v % of 3.97 DE dextrin, 12.7 g/v % of $KH_2PO_4$ and 18.6 g/v % of $K_2HPO_4$. The amount of glucose-1-phosphate synthesized was measured at the outlet of the column. The results are shown in Table 1, which demonstrates consistent production of glucose-1phosphate for a period of at least 70 days.

TABLE 1

| Days | Amount of glucose-1-phosphate produced (mmol/l) |
|---|---|
| 0 | 0 |
| 5 | 186.5 |
| 9 | 185.3 |
| 15 | 193.0 |
| 21 | 186.0 |
| 27 | 188.3 |
| 30 | 190.5 |
| 35 | 192.3 |
| 40 | 189.0 |
| 44 | 187.8 |

TABLE 1-continued

| Days | Amount of glucose-1-phosphate produced (mmol/l) |
|---|---|
| 50 | 187.3 |
| 55 | 190.4 |
| 63 | 186.9 |
| 70 | 186.8 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent:

1. An immobilized phosphorylase, prepared by contacting a solution of unrefined potato juice containing phosphorylase enzyme with an anion-exchange resin which is a synthetic crosslinked styrene polymer having trimethylammonium anion exchange groups.

2. The immobilized phosphorylase of claim 1, wherein the amount of phosphorylase immobilized on said resin is such that the ratio of the total activity (U) of phosphorylase to the weight of anion exchange resin (g) is greater than 5.0 (U/g).

3. The immobilized phosphorylase of claim 1, wherein said contacting comprises passing said unrefined potato juice through a column packed with said anion-exchange resin.

4. The immobilized phosphorylase of claim 1, wherein said contacting comprises shaking for about 5 hours.

5. The immobilized phosphorylase of claim 1, wherein an amount of from 3.5 to 60 ml of said unrefined potato juice is contacted per gram of said anion-exchange resin.

* * * * *